(12) United States Patent
Schneider et al.

(10) Patent No.: US 7,272,250 B2
(45) Date of Patent: Sep. 18, 2007

(54) VESSEL SEGMENTATION WITH NODULE DETECTION

(75) Inventors: Alexander C. Schneider, Sunnyvale, CA (US); Susan A. Wood, Mountain View, CA (US)

(73) Assignee: R2 Technology, Inc., Santa Clara, CA (US)

( * ) Notice: Subject to any disclaimer, the term of this patent is extended or adjusted under 35 U.S.C. 154(b) by 0 days.

(21) Appl. No.: 09/993,791

(22) Filed: Nov. 23, 2001

(65) Prior Publication Data

US 2002/0090121 A1 Jul. 11, 2002

Related U.S. Application Data

(60) Provisional application No. 60/252,743, filed on Nov. 22, 2000, and provisional application No. 60/314,582, filed on Aug. 24, 2001.

(51) Int. Cl.
*G06K 9/10* (2006.01)

(52) U.S. Cl. ...................................... 382/128; 600/481

(58) Field of Classification Search .................. 382/100, 382/154, 128–134, 171–173; 345/766; 378/4, 378/37, 62; 660/407, 425, 437; 664/28; 600/481
See application file for complete search history.

(56) References Cited

U.S. PATENT DOCUMENTS

| | | | | | |
|---|---|---|---|---|---|
| 4,523,596 A | * | 6/1985 | Macovski | .................... | 600/413 |
| 4,945,478 A | * | 7/1990 | Merickel et al. | ............ | 382/131 |
| 5,003,979 A | * | 4/1991 | Merickel et al. | ............ | 600/410 |
| 5,273,040 A | * | 12/1993 | Apicella et al. | ............ | 600/410 |
| 5,365,429 A | * | 11/1994 | Carman | ........................ | 378/37 |
| 5,627,907 A | * | 5/1997 | Gur et al. | .................... | 382/132 |
| 5,803,914 A | * | 9/1998 | Ryals et al. | ................. | 600/407 |

OTHER PUBLICATIONS

Herk et al., Automatic three–dimensional correlation of CT–CT, CT–MRI, and CT–SPECT using Chamfer matching, Medical Physics, vol. 27, No. 7, Jul. 1994, pp. 1163–1178.*

Collignon et al., Automated Multi–Modality Image Registration Based on Information Theory, Imformation Processing in Medical Imaging, 1995, pp. 263–274.*

Hibbard et al., Three–Dimensional Representation and Analysis of Brain Energy Metabolism, Siemend Medical Systems, Jun. 26, 1987, pp. 1641–1646.*

Kawata et al., Surrounding Structures Analysis of Pulmonary Nodules Using Differential Geometry Based Vector Fields, IEEE 2000, pp. 424–427.*

* cited by examiner

*Primary Examiner*—Jayanti K. Patel
(74) *Attorney, Agent, or Firm*—Morgan, Lewis & Bockius LLP

(57) ABSTRACT

A region-growing method for identifying nodules in an anatomical volume segments a 3-D image volume by controlled voxel growth from seed points. The process is based on creation and use of a distance map for tracking the distance of vessel voxels from a predetermined location. A volume map is created that identifies the largest sphere that can pass between a voxel and a predetermined location without touching a non-vessel voxel. The ratio between the distance map and the volume map is analyzed to find regions more likely to contain nodules, the features of which can be extracted or otherwise highlighted.

24 Claims, 11 Drawing Sheets

VESSEL SEGMENTATION WITH NODULE DETECTION

CROSS-REFERENCE TO RELATED APPLICATIONS

Related applications are:

"Density Nodule Detection in 3-Dimensional Medical Images," Ser. No. 09/993,792, filed concurrently herewith;

"Method and System for the Display of Regions of Interest in Medical Images," Ser. No. 09/990,508, filed Nov. 21, 2001, attorney docket number 8498-039-999;

"Automated Registration of 3-D Medical Scans of Similar Anatomical Structures," Ser. No. 09/993,790, filed concurrently herewith;

"Lung Field Segmentation From CT Thoracic Images," Ser. No. 09/993,793, filed concurrently herewith;

"Pleural Nodule Detection from CT Thoracic Images," Ser. No. 09/993,789, filed concurrently herewith; and "Graphical User Interface for Display of Anatomical Information," Ser. No. 09/990,511, filed Nov. 21, 2001, claiming priority from Ser. No. 60/252,743, filed Nov. 22, 2000 and from Ser. No. 60/314,582 filed Aug. 24, 2001.

This application hereby incorporates by reference the entire disclosure, drawings and claims of each of the above-referenced applications as though fully set forth herein.

FIELD OF THE INVENTION

The present invention relates to feature extraction and identification by segmenting an image volume into distinctive anatomical regions. The invention further relates to methods for identifying nodules in segmented images.

BACKGROUND OF THE INVENTION

The diagnostically superior information available from data acquired from various imaging systems, especially that provided by multidetector CT (multiple slices acquired per single rotation of the gantry) where acquisition speed and volumetric resolution provide exquisite diagnostic value, enables the detection of potential problems at earlier and more treatable stages. Given the vast quantity of detailed data acquirable from imaging systems, various algorithms must be developed to efficiently and accurately process image data. With the aid of computers, advances in image processing are generally performed on digital or digitized images.

Digital acquisition systems for creating digital images include digital X-ray film radiography, computed tomography ("CT") imaging, magnetic resonance imaging ("MRI") and nuclear medicine imaging techniques, such as positron emission tomography ("PET") and single photon emission computed tomography ("SPECT"). Digital images can also be created from analog images by, for example, scanning analog images, such as typical x-rays, into a digitized form. Further information concerning digital acquisition systems is found in our above-referenced copending application "Graphical User Interface for Display of Anatomical Information".

Digital images are created from an array of numerical values representing a property (such as a grey scale value or magnetic field strength) associable with an anatomical location referenced by a particular array location. In 2-D digital images, or slice sections, the discrete array locations are termed pixels. Three-dimensional digital images can be constructed from stacked slice sections through various construction techniques known in the art. The 3-D images are made up of discrete volume elements, also referred to as voxels, composed of pixels from the 2-D images. The pixel or voxel properties can be processed to ascertain various properties about the anatomy of a patient associated with such pixels or voxels.

Once in a digital or digitized format, various analytical approaches can be applied to process digital anatomical images and to detect, identify, display and highlight regions of interest (ROI). For example, digitized images can be processed through various techniques, such as segmentation. Segmentation generally involves separating irrelevant objects (for example, the background from the foreground) or extracting anatomical surfaces, structures, or regions of interest from images for the purposes of anatomical identification, diagnosis, evaluation, and volumetric measurements. Segmentation often involves classifying and processing, on a per-pixel basis, pixels of image data on the basis of one or more characteristics associable with a pixel value. For example, a pixel or voxel may be examined to determine whether it is a local maximum or minimum based on the intensities of adjacent pixels or voxels.

Once anatomical regions and structures are constructed and evaluated by analyzing pixels and/or voxels, subsequent processing and analysis exploiting regional characteristics and features can be applied to relevant areas, thus improving both accuracy and efficiency of the imaging system. For example, the segmentation of an image into distinct anatomical regions and structures provides perspectives on the spatial relationships between such regions. Segmentation also serves as an essential first stage of other tasks such as visualization and registration for temporal and cross-patient comparisons.

One application of digital acquisition systems is detection and confirmation of cancer, cancerous nodule or disease. Unfortunately, in all too many cases, this application is merely to confirm the worst. By the time a patient has symptoms enough that warrant the use of digital acquisition systems, the cancer or disease detected by digital acquisition systems may have progressed to the point that the patient is almost certain to die or faces irreversible or interminable illness. It is desirous to find a cost-effective way to use digital acquisition systems as a screening device to detect cancer or disease at an early and treatable stage.

One technique of image processing is known as "volume growing" or "region growing". Region growing techniques, as opposed to edge-based segmentation techniques, are particularly effective in noisy images since edges in noisy images are extremely difficult to detect. In region growing, generally a seed voxel, or volume element, is identified within an anatomical structure of interest. Growth from a seed voxel is controlled by adding voxels so long as the resulting region or chain, or tree, of voxels generally remains within prescribed limits.

Key issues in digital image processing are speed and accuracy. For example, the size of a detectable tumor or nodule, such as a lung nodule, can be smaller than 2 mm in diameter. Moreover, depending on the particular case, a typical volume data set can include several hundred axial sections, making the total amount of data 200 Megabytes or more. Thus, due to the sheer size of such data sets and the desire to identify small artifacts, computational efficiency and accuracy is of high priority to satisfy the throughput requirements of any digital processing method or system.

SUMMARY OF THE INVENTION

The present invention is a system for efficiently detecting and highlighting anatomical information obtained from a digital acquisition system. In particular, seeds are identified and grown into regions in a controlled manner. The regions processed to highlight potentially cancerous nodules and other particles or objects.

BRIEF DESCRIPTION OF THE DRAWINGS

These and other objects, features and advantages of the invention will be more readily apparent from the following detailed description of the invention in which.

DETAILED DESCRIPTION OF THE INVENTION

Modern CT scanners, particularly multidetector scanners which acquire more than one slice per gantry rotation, provide structural data of unprecedented quality due to their favorable volumetric resolution and acquisition speed. This data has superior diagnostic value, enabling the detection of potential cancers or other health problems at early and more treatable stages. Similarly, detecting a particle or obstacle that can restrict the flow of blood is helpful in assessing the health of a patient regarding the adequate flow of blood to vital organs.

Figure 1:
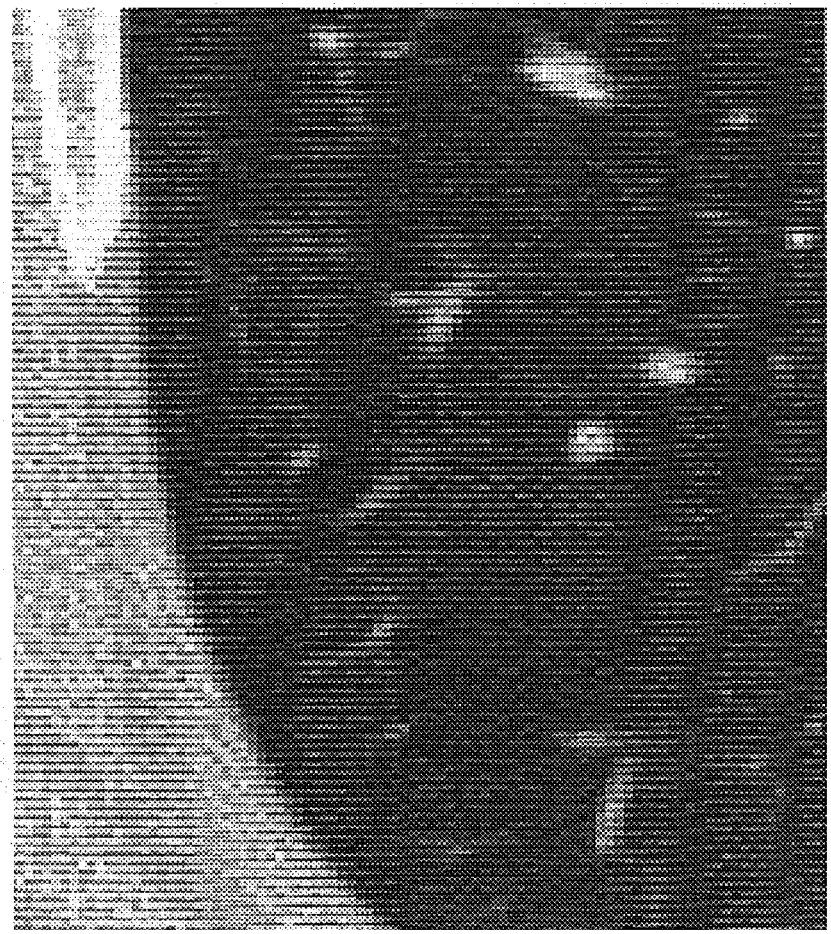
FIG. 1 depicts an axial CT section of a digital thoracic image with various vessel cross-sections and particles shown.

Within various images of the anatomy, such as images including the lungs or the heart or portions thereof, numerous grey flecks may appear on a CT axial scan or other digital image. For the most part, these flecks may be sections of blood vessels that have absorbed sufficient x-rays to be visible in the grey scale image. FIG. 1 depicts a digital axial section of a thoracic region with various visible cross-sections of blood vessels scattered throughout the image. These vessels can be identified by finding contiguously aligned flecks in adjacent axial or other planar sections and following such structures through the planar sections long enough to establish that they are indeed sections of blood vessels. Some flecks, however, may be cancerous nodules or particles capable of restricting blood flow in blood vessels or to organs. For example, potentially cancerous nodules are generally recognizable by their globular shape and their isolation from other anatomical structures. Nonetheless, successfully detecting nodules can be difficult due to the subtlety of nodules themselves, the similarity of the nodules to normal anatomic information in the nodule background and background image noise.

A region-growing (or volume-growing) approach applied to a series of digital anatomical images can assist in separating blood vessels from possible nodules. Further processing can assist in the identification of potentially cancerous or troublesome nodules in an anatomic system. For region-growing, generally a 3-D seed voxel, or volume element, is identified within the anatomical structure of interest. A region is grown from the seed voxel (or volume element) by adding neighboring pixels (or voxels) that are similar, increasing the size of the region. In region-growing about a seed voxel, nearby voxels are successively analyzed and identified as belonging to the same structure if such voxels adjoin a voxel already identified as belonging to the structure and if the voxels satisfy a condition generally representative of some physical attribute or other processing characteristic. In various region-growing methods, a volume element is identified as a seed, and some number of nearby voxels are analyzed to determine whether such adjacent volume is to be considered as associated with the seed voxel for further processing. Whether a nearby voxel is to be considered part of the region grown from the seed is generally depends upon a determination whether an attribute associated with a candidate voxel is within a specified range of values. If so, such adjacent voxels are marked as belonging to the structure "grown" from the seed.

Figure 2:
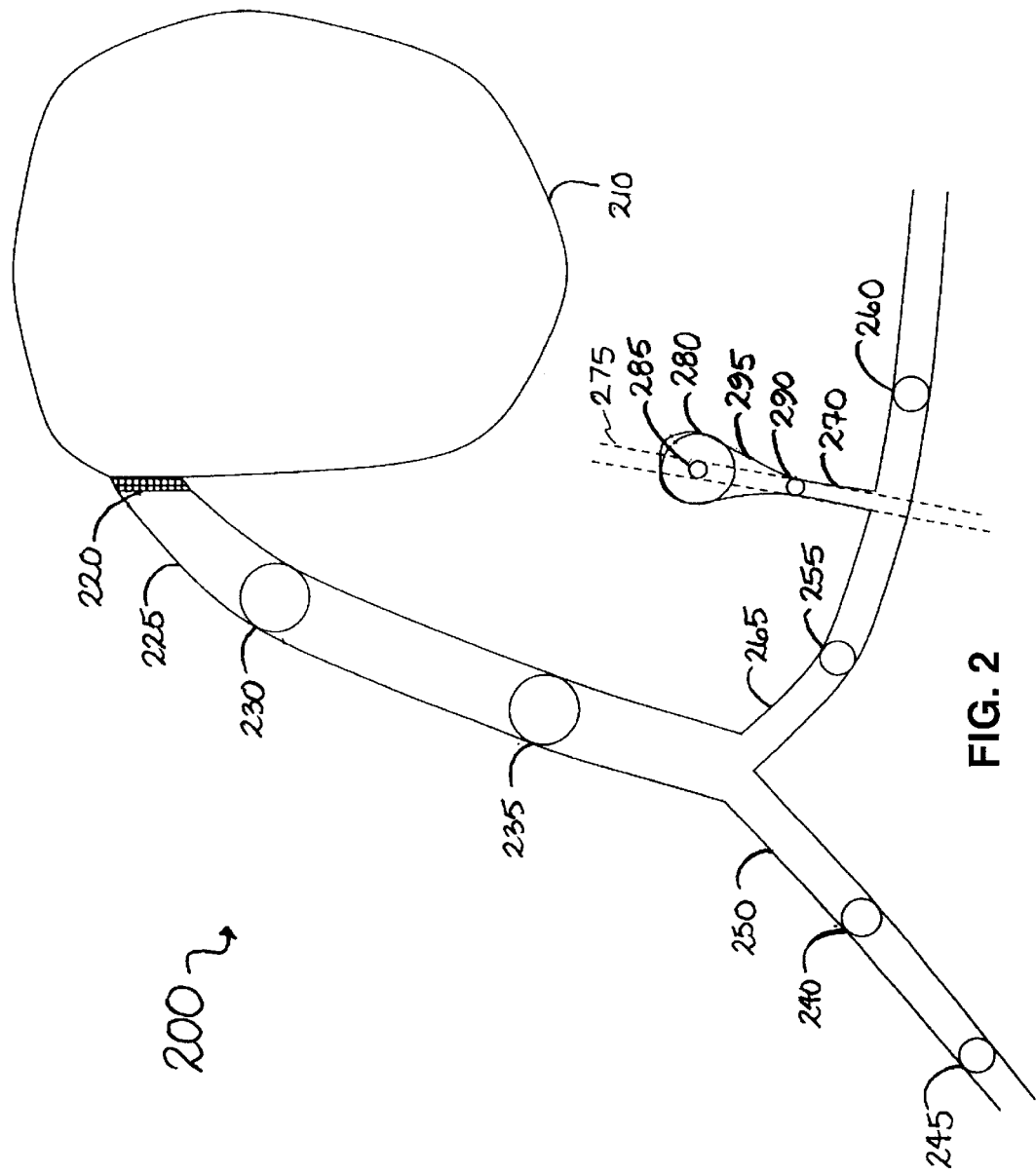
FIG. 2 is a representation of voxel seeds applied for growing vessels near a heart.

FIG. 2 is a schematic representation of a digital image of a heart and circulatory system 200 useful in further description of an embodiment of the present invention. The system includes a heart 210 for circulating blood through various blood vessels, such as vessels 225, 250, 265 and 270. As can be seen in FIG. 2, the vessels can vary in diameter and length. In a healthy body, a blood vessel that originates at the heart 210 is larger in diameter than vessels that ultimately branch from it. As blood vessels carry blood further from the heart, vessels branch into smaller diameter vessels. For example, vessel 225 is shown originating from the heart and branching into smaller vessels 250 and 265. Vessel 270 is shown branching from a larger vessel 265. Similarly, vessels returning blood to the heart combine to form larger and larger vessels as they get closer to the heart.

In a region-growing approach, the widths of various vessels can be determined at various locations along a particular vessel or vessel segment. Each width corresponds to the radius of the largest sphere that can pass through the vessel at that location. For example, for vessel 225, vessel widths 230 and 235 correspond to particular widths along the vessel. Similarly, vessel 250 has vessel widths at 240 and 245 that correspond to the largest sized particle that can pass at their respective locations. Vessel 265 has vessel widths at 255 and 260 that correspond to the largest sized particle that can pass at their respective locations. As shown, vessels 225, 250 and 265 are healthy vessels as the vessel width along each vessel is relatively even and smooth. Vessel 270 is shown having a vessel width 290. In a normally healthy vessel, the width of vessel 270 would remain approximately that of width 290 out towards location 275. However, a bulge 280 having a diameter greater than the effective vessel width 290 is shown in vessel 270. The bulge represents a candidate location for further analysis.

While bulge 280 could be internal to the vessel and caused by an aneurysm, it might also be due to the presence of a nodule external to vessel 270. Distinguishing nodules from vessels in digital images is difficult. Nodules often appear on digital images as having the same density of a blood vessel. Since pixels of nodules in a digital image are very similar to pixels of vessels, information from pixels containing nodule information can be combined with information relating to vessels, resulting in an apparent vessel bulge in one or more views. If the vessel itself is actually bulging due to the presence of a particle inside the vessel, there is often a taper 295 associated with an actual vessel bulge. However, given the possible non-uniform and globular shape of nodules, a taper 295 may still appear in a particular view caused by the presence of an external nodule. Additionally, bulge 280 may actually be a particle restricting flow of blood to and from the heart and to or from the anatomical region served by vessel 270. Whether an aneurysm, blockage or a nodule, the apparent bulge region is certainly a candidate for further investigation.

In one embodiment of the present invention, seed voxels for region-growing are shown at 220, where blood vessels originate from or terminate at the heart 210. The seed voxels can be grown into blood vessel trees by way of various region-growing approaches known in the art. Tracking of various vessel widths as determined by a region-growing approach can be used to identify possible nodules external to but touching an actual vessel. A nodule appearing attached to a vessel causes the width of the vessel to appear to increase at the location of nodule attachment. The similarity of vessel voxels to nodule voxels causes the region-growing algorithm to make a blood vessel appear to grow in width (in the case of blood flow away from the heart) or possibly appear as a vessel shrinkage (for flow to the heart).

The application of a region-growing approach described herein is effective in any portion of the anatomy containing distinct blood vessels, particularly the thoracic region. Since much of the lungs is comprised of blood vessels and air sacs, edges are often more clearly defined and vessels and nodules are generally more readily apparent against the lung tissue and background. Accordingly, in one approach vessel 225 can be a vessel providing blood to the lungs, and vessels 250 and 265 can provide blood to a respective lung. By continuing a region-growing approach from the vessels providing blood to the lungs, the smaller blood vessels of the lungs can be identified. Also, given the density of fine vessels and capillaries throughout the lungs, chances are high that nodule information on an image would appear to show the nodule "touching" a blood vessel or capillary.

Figure 3:
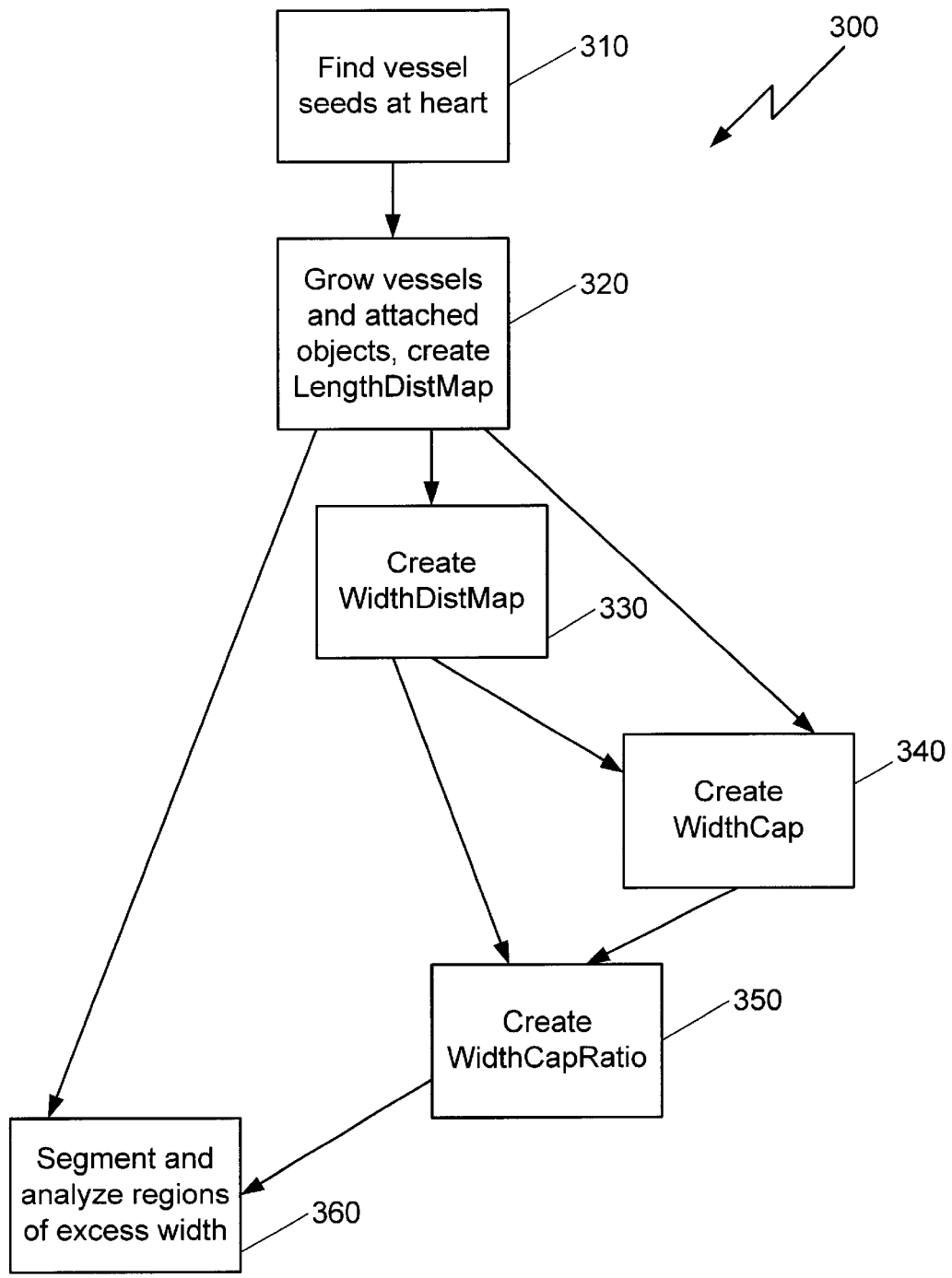
FIG. 3 is a process flow chart of the vessel growing and nodule detection approach in accordance with the invention
Figure 4:
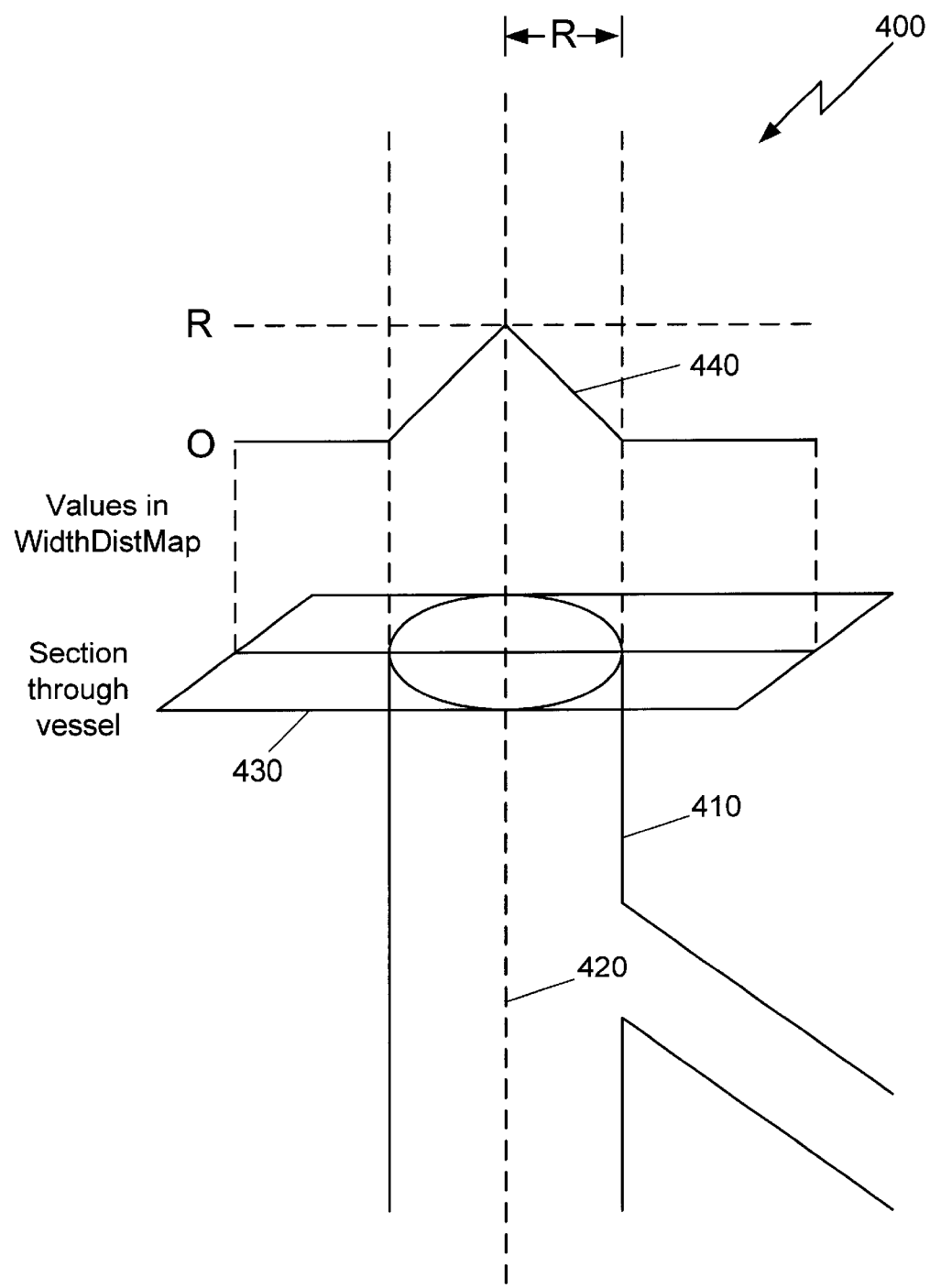
FIG. 4 is a width distance map generated in accordance with one aspect of the invention.

FIG. 3 represents a process flow chart 300 of a vessel growing and nodule detection approach in accordance with the invention. The process flow can be adapted to various anatomical systems such as system 200 or other anatomical regions including, without limitation, the heart, brain, spine, colon, liver and kidneys. For illustrative purposes, the digital processing approach is described with respect to system 200. As applied to the heart, the regions grown correspond to blood vessels of a circulatory system.

Region-growing begins by identifying candidate seeds at step 310. In one approach of the present invention, seeds to be used in growing blood vessels are found where vessels join a heart-based portion of an anatomy. In other words, a voxel is selected as a seed voxel if the voxel is part of a blood vessel and that voxel has at least one adjacent voxel face that is located on, or associated with heart 210. Seed voxels may also be selected as those voxels having a certain threshold intensity located in a anatomic field region and which have at least one adjacent voxel that is located on, or associated with, heart 210.

In yet a further embodiment, a seed voxel is selected on the basis whether the voxel has at least one adjacent voxel that is located on, or associated with, a heart region 210 and is within a geometric volume that is positioned and sized relative to the lungs to contain roots of blood vessel trees. These seeds form sheets that cut a vessel at its junction with a non-lung based portion of the anatomy, such as a heart. To attain reasonable processing efficiency, a predetermined threshold size for the geometric volume is selected. A lower threshold size of the geometric volume element results in higher sensitivity and resolution in processing. However, too low a threshold adds to computation burden. A geometric volume selected as an ellipsoid yields effective results in many cases. For detection over a smaller region, smaller ellipsoidal dimensions can be effective since processing computations are performed over a limited area, and therefore, the computational burden is not as large as performing the same processing over a larger region. In other embodiments, larger ellipsoidal radii can be used to select regions of interests, which may then be further processed with smaller ellipsoids, or other geometric shapes such as spheres or boxes. In other implementations, a single geometric structure may be used, based on knowledge of the region being processed.

At step 320, once a seed voxel is identified, adjacent voxels are added to the seed volume if such adjacent voxels satisfy a predetermined condition. Each voxel added to a volume growth is itself processed like a seed voxel, with adjoining voxels analyzed to determine whether their physical attributes are within a prescribed range. This process continues, each iteration adding a volume of further acceptable voxels to a growth structure having evolved from the seed voxel.

Sets of voxels grown from seed voxels create volumes of the anatomical structure being analyzed. As applied to thoracic regions, vessel seeds can be grown to mirror blood vessels in the lung. Growth of adjacent voxel volumes continues until growth in every direction is stopped by an absence of voxels meeting specified physical criteria.

In one embodiment, vessel seeds are used to grow contiguous voxels that have values greater than a threshold intensity level. In a further refinement, the intensity values are smoothed. Further information concerning digitally segmenting, identifying and processing thoracic surfaces can be found, for example, in the above-referenced application "Density Nodule Detection in 3-Dimensional Medical Images". In yet a further embodiment, a set of grown voxels is used to seed the growth of attached voxels that exceed a predetermined intensity threshold level in a Laplacian-of-Gaussian ("LoG") volume. LoG operations typically reduce the magnitude of noise in image datasets while keeping edges relatively sharp. By reducing such noise, it is easier to segment smaller vessels cleanly. Various LoG edge detection operators are known in the prior art, for example where Gaussian-shaped smoothing is performed prior to the application of a Laplacian function.

As various vessels are generated from seed voxels (i.e., as a vessel tree is generated), an array is created which tracks the distance of each voxel from a seed location. In one embodiment applied to the lungs, a length-distance array is created that tracks the distance of each voxel from the heart, or from seed voxels described above. For the length-distance array, a value would be zero for the seed voxel and appropriately and correspondingly increase for voxels further away from the heart, such as along the length of the growth region, or vessel.

As noted above, since nodules in a digital image often appear very similar to vessels, information from pixels containing nodule information can be combined with information relating to vessels, resulting in the apparent variations in vessel widths. The variation in vessel widths can be mapped and analyzed for purposes of identifying candidate nodules or regions of interest for further evaluation and consideration.

An array 400 is produced at step 330 which has as elements the value zero for any non-vessel voxel and a value for each vessel voxel in a grown region is that is proportional to the distance of that voxel to the nearest non-vessel voxel. As a result, along the center 420 of each vessel 410 in array 400 there is a ridge 440 whose height is directly proportional to the radius, R, of the vessel 410 at a particular planar section 430. A voxel located at the center 420 will have a value associated with it that is equal to the radius, R, of the vessel at that location. The array 400 is referred to as the width-distance arry.

Figure 5:
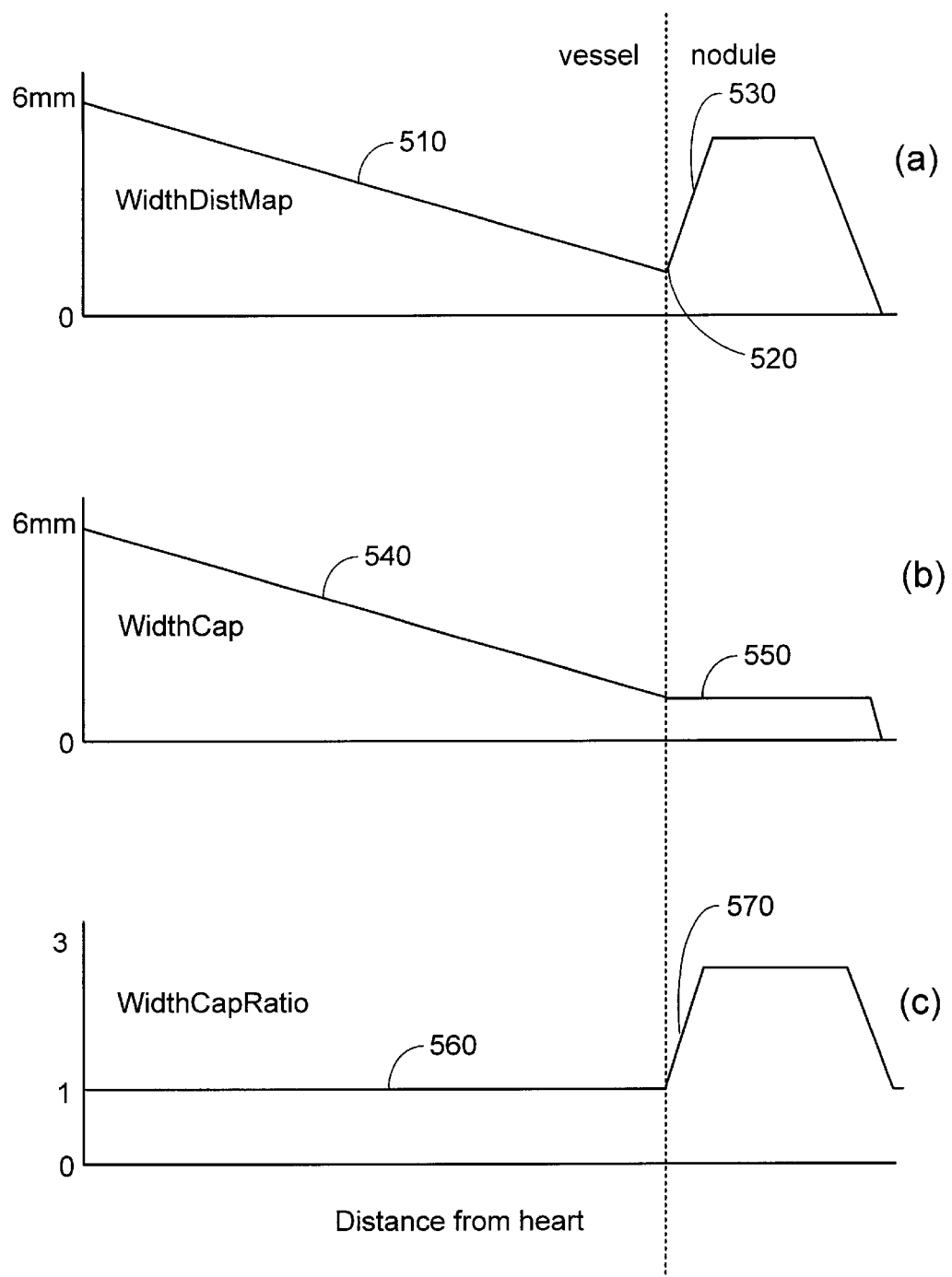
FIG. 5(a) is map of the width-distance generated in accordance with one aspect of the invention.
FIG. 5(b) is map of the WidthCap values generated in accordance with one aspect of the invention.
FIG. 5(c) is map of the ratio of the width-distance to the WidthCap values generated in accordance with one aspect of the invention.

A sample profile of a width-distance array is provided in FIG. 5(a). Segment 510 represents the height of ridge 440. In general, the height of ridge 440 decreases with increasing distance from the heart as indicated by the downwardly sloping line segment 510. At point 520, however, a nodule is assumed to be attached to the vessel, such that the radius of the vessel increases rapidly as indicated by line segment 530. Segment 510 is not generally a straight line having the constant slope shown in FIG. 5, but is often piecewise constant, decreasing abruptly when a vessel branches into smaller vessels.

The next steps in the process flow 300 relate to finding and marking nodule candidates in vessel trees grown in step 320. The process flow 300 utilizes information from the length-distance array created at step 320 to identify at step 340 a set of vessel voxels S that are within a prescribed distance from the heart.

At step 340, the maximum value in the width-distance array from step 330 associated with the vessel voxels S is set as the Max_Width_Threshold and the minimum value in the width-distance array from step 330 associated with the vessel voxels S is set as Min_Width_Threshold. A variable, width_threshold, is initialized to the Max_Width_ Threshold value and iteratively decreased until the value of width_threshold reaches the Min_Width_Threshold. During the iteration process, for each value of width_threshold, S is expanded to include any voxel adjacent to a voxel in S whose value in the width-distance array is greater or equal to width_threshold, and each newly added voxel is given the current value of width_threshold. During the iteration process, new voxels for the set S can be identified and obtained from the length-distance array. The value assigned a given vessel voxel is proportional to the radius of the largest sphere that can pass between that voxel and the heart without touching a non-vessel voxel. The process at step 340 effectively captures the width of the narrowest constriction between the given voxel and predetermined region (the "WidthCap value"), such as the heart. A sample profile of WidthCap values is provided in FIG. 5(b). Segment 540 corresponds to vessel widths of a healthy vessel segment having no nodules attached thereto. However, at the point where a nodule is attached (thereby increasing the vessel width), the WidthCap value for segment 550 will not increase. For example, a nodule with a radius of 3 mm attached to a 1 mm radius vessel will not have a WidthCap value greater than 1 mm. Instead, the width of the nodule is captured in the width-distance array of step 330.

Once the WidthCap values are created at step 340, a ratio of the corresponding values in the width-distance array to their corresponding WidthCap values can be taken at step 350. For such a ratio, non-vessel voxels have a value of zero. Within the vessels, the minimum, and most common, value is 1. Ratios greater than '1' indicate a region of a greater than expected radius, or a "bulge". A profile of the ratio can be seen in FIG. 5(c) where the ratio is '1' along segment 560 until the point where the ratio is above '1' along segment 570, and hence, the "bulge" created in the profile.

Figure 6:
FIG. 6 depicts the axial section of FIG. 1 as processed in accordance with an embodiment of the present invention wherein the vessels are removed and a nodule candidate remains.

Once the ratios are taken at step 350, nodule candidates can be selected at step 360. Contiguous regions of voxels with ratios computed at step 350 of more than '1' can be segmented and analyzed with respect to various features to identify regions more likely to be nodules as opposed to, for example, stretches of vessels downstream of an artificial constriction caused by an artifact of a vessel-growing method. Some features used for selection of contiguous regions as candidate nodules include the ratio determined at step 350, the difference of the maximum and minimum length-distance array values determined at step 320, the distance from the most downstream point in a region to the end of a vessel, and the volume of the region. Selected regions of excess width can be identified or highlighted. A restored nodule from the axial image of FIG. 1 can be seen in FIG. 6.

While ratios are taken at step 350, it is possible to obtain similar results without taking the ratio or creating the second array of values. In one approach, slopes of the widths of a single vessel can be processed simply to identify possible maxima and minima associated with a change in slopes. Such a change in slope can be indicative of vessel narrowing in a region where a vessel is expected to continue to broaden or can be indicative of vessel broadening where a vessel was expected to continue to narrow.

In another aspect of the present invention, once a region-growing procedure has identified various vessel pixels or voxels, such vessels can be removed from a digital image or image data set. This removal of the vessels is possible since pixels and/or voxels have been identified by a region-growing technique and can effectively be removed or ignored in further processing, particular if the vessels do not appear as unhealthy or having possible nodules. By removing vessel pixels or voxels from data images, or ignoring such pixels or voxels in further processing, the remaining portion of the images or volumes can be processed separately, thereby reducing computational burden and permitting any remaining image portion to be processed further. For example, various segmentation or smoothing operations can be performed on the remaining anatomy to detect abnormalities or unhealthy tissue.

The present invention is also highly effective when used with or applied to an angiocardiographic procedure. In such a procedure, a contrast medium is injected into an artery or vein, or introduced into a catheter inserted in a peripheral artery and threaded through the vessel to a particular site. Advantageously, when a contrast medium or dye is injected into the heart or blood vessels, the contrast medium makes the vessels more intense and/or more defined in x-rays or images obtained from various imaging systems. An angiocardiographic procedure can often be easily performed at the same time typical digital images are obtained from a digital acquisition system.

In areas of possible blockage in both analog and digital angiograms, the contrast media appears less bright and less intense. Since the angiogram can be acquired in a digital or digitized form, the results of a region-growing algorithm can be used to map or compare against the trace or outlines of the blood vessels and organ chambers identified by the angiogram. Results of an angiogram can be combined with detailed computer results of the region-growing procedure to identify areas of possible blockage, possible aneurysm locations, identify possible embolisms and other health problems associated with vessel blockage. While the results of angiograms generally are simply visually processed by medical personnel, the ability to process with a computer the results of the region-growing procedure with the angiogram makes it possible to identify ROIs that may otherwise be overlooked. Additionally, possible areas of concern can be highlighted on digital angiograms to assist with identification and facilitate medical diagnosis.

Figure 7:
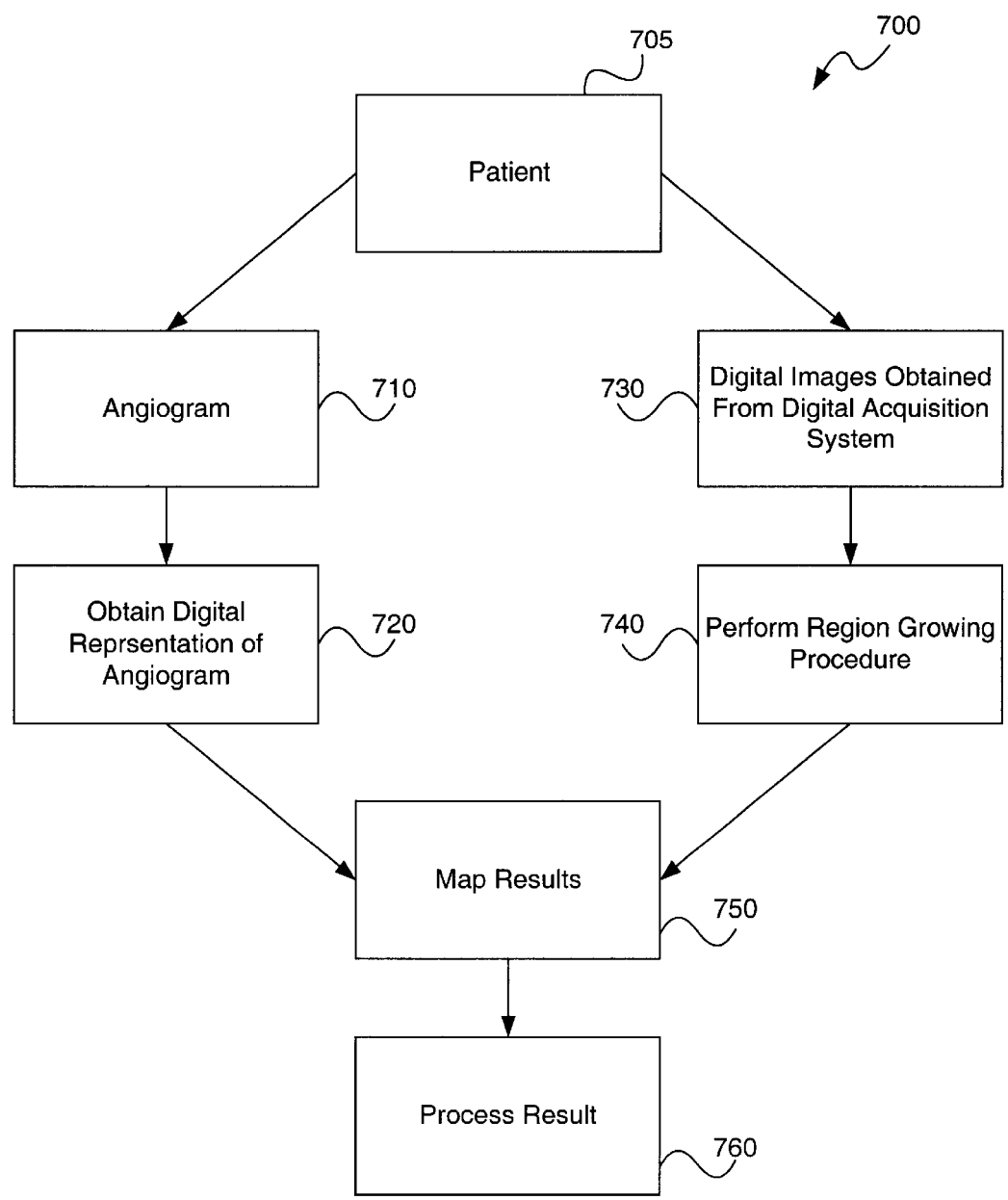
FIG. 7 depicts a process flow chart for processing the results of vessel growing against the results of an angiocardiographic procedure.

FIG. 7 represents one process for combining separate results from an angiocardiographic procedure with information obtained from a digital acquisition system. In process 700, an angiogram 710 of a patient is obtained by a standard angiocardiographic procedure. The angiogram is converted to or obtained as a digital or digitized image at step 720. Pixel or voxel data obtained from step 720 representative of pixel or voxel intensities are stored for use in a digital comparison or mapping at step 750.

Images of the patient are also detected from a digital acquisition system at step 730. Various region-growing procedures performed at step 740 on the digital data obtained from the digital images at step 740. The results of the pixel or voxel data obtained from step 720 are compared to the results of the pixel or voxel data obtained from region-growing procedure. The results are processed at step 760 based on differences identified at the mapping or comparison step 750. For example, the results from the angiogram might not show sufficient contrast media at a particular location. The absence or faint appearance of a blood vessel in an angiogram may go unnoticed. However, the results of the region-growing would show voxels of a vessel in a location not detected in the angiogram. Various comparison techniques in the art can be used to highlight differences in results obtained from the angiogram and from the region-growing procedure. These differences can alert doctors to potential problem or areas requiring further investigation or testing.

Figure 8:
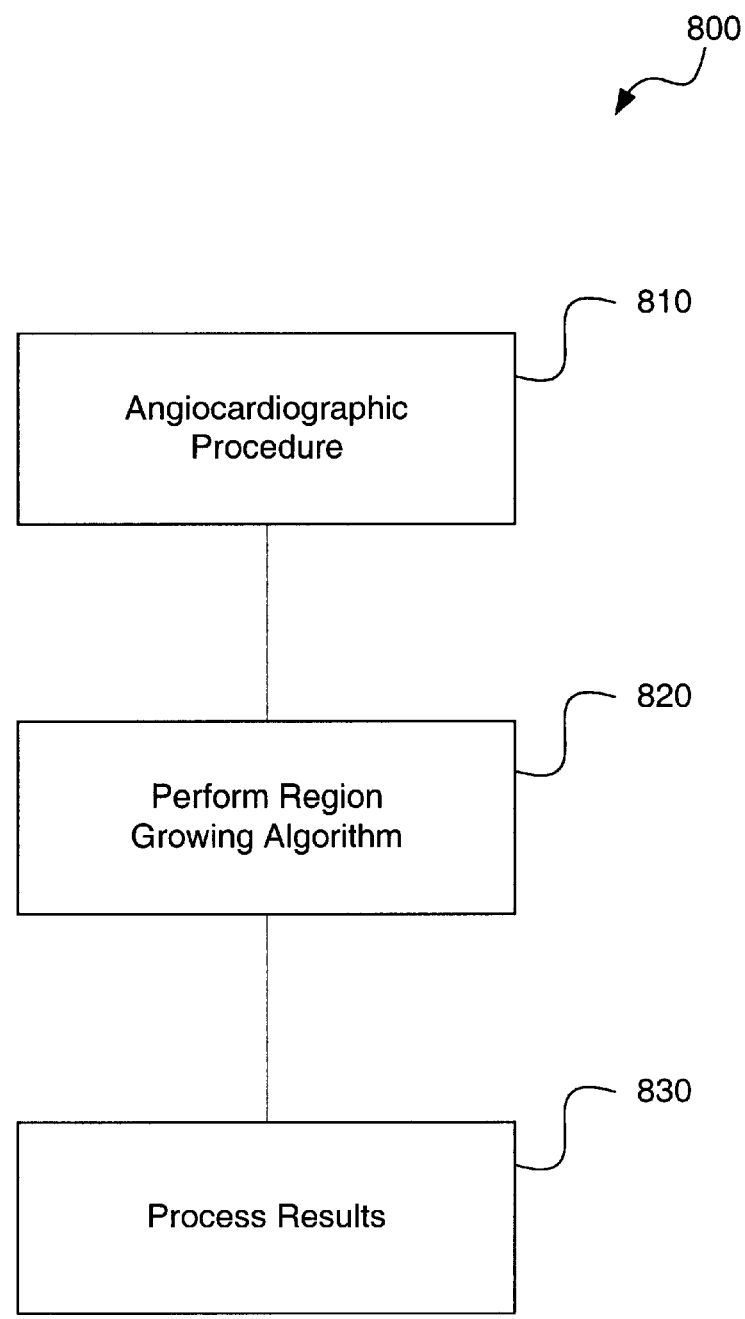
FIG. 8 depicts a process flow chart for processing the results of vessel growing.

While process 700 depicts the angiogram 710 being obtained distinctly and separately from digital image processing performed at step 730, FIG. 8 shows a process 800 where the region growing procedure is performed directly on the results from a angiocardiographic procedure. For example, an angiocardiographic procedure is performed on a patient at step 810. The procedure results in a digital or digitizable angiogram. Image intensities associated with pixels or voxels of the angiogram are stored. At step 820, region growing is performed directly on the angiocardiographic data or on digital images obtained from the angiocardiographic procedure. For example, seed pixels or voxels are identified and grown in accordance with certain criteria. The region-growing procedure is used to provide data to compare or check against the angiogram. Step 830 is used to highlight differences in the result obtained from the angiogram and from the results obtained by the region-growing procedure. Highlighted differences can be indicative of arterial blockages, possible aneurysms or other possible circulatory problems.

The processes identified in FIGS. 7 and 8 can be used as a diagnostic aid in a variety of applications, including, without limitation, in myocardial infarction, vascular occlusion, calcified atherosclerotic plaques, cerebrovascular accident, portal hypertension (e.g., from liver failure), kidney neoplasms, renal (kidney) artery stenosis as a causative factor in hypertension, pulmonary emboli, and congenital and acquired lesions of pulmonary vessels. Cerebral angiography is used to demonstrate the presence of an aneurysm within the brain or to help visualize a brain tumor prior to surgery. The present invention is effective with these and other procedures.

The methods described herein do not require the explicit segmentation of vessel segments, branches or any other structures within the vessel trees. Thus, the methods are considered robust and does not pose a significant computational burden. The methods can also result in the detection of non-vascular structures such as nodules, airway walls, atalectesis (local collapse), thickened fissures and fluid collected in the posterior portion of a lung.

Figure 9A:
FIG. 9(a) is a digital image showing various vessels with possible nodule candidate.
Figure 9B:
FIG. 9(b) is the digital image of FIG. 9(a) with vessels and nodules removed.
Figure 9C:
FIG. 9(c) is the digital image of FIG. 9(b) with restored nodules in accordance with the present invention.

FIG. 9(a) is a representative digital image to be processed in accordance with the invention. The region-growing procedure in accordance with the invention is applied to the image in FIG. 9(a) to generate the image in FIG. 9(b) by removing pixels associated with vessels and nodules. FIG. 9(c) is the digital image of FIG. 9(b) with nodules identified and restored in accordance with another aspect of the present invention.

The approaches described herein enhance the diagnostic value of the scans obtained from digital acquisition systems as well as enable the diagnostic determination by a physician in the effort to detect abnormalities at early and curable stages. Potentially unhealthy tissue is identified or otherwise highlighted for a region where, in prior approaches, such unhealthy tissue may go undetected or unnoticed. Pre- and post-processed images can be compared in a registration system. In addition, images taken at different times can be processed so as to monitor progression of a nodule or other regions of interest.

As will be apparent to those skilled in the art, numerous modifications may be made in the display of the present invention that are within the scope and spirit of the invention. While the invention has been described in a particular context of CT scanning of the lungs to detect potentially cancerous regions, the invention may also be used to display the results of digital scanning of other regions of the body and for other applications as well as to display the results of other digital acquisition systems.

What is claimed:

1. A method for detecting a candidate nodule from anatomical images comprising the steps of:

selecting a seed voxel from a volume created from the anatomical images;

growing a region from the seed voxel, said region defined by a volume made up of voxels contiguous to the seed voxel and satisfying growth criteria;

creating a first array having first array values that relate each voxel of the region to a first voxel distance;

creating a second array having second array values that relate each voxel of the region to a second voxel distance; and processing a ratio of a first array value to a corresponding second array value to determine a candidate nodule location.

2. The method of claim 1 wherein the seed voxel is part of a blood vessel.

3. The method of claim 1 wherein the seed voxel is part of a blood vessel and at least one voxel face is associated with a heart or heart region.

4. The method of claim 1 wherein the seed voxel exceeds a threshold intensity level.

5. The method of claim 1 wherein the seed voxel is selected within a geometric volume containing roots of blood vessel trees.

6. The method of claim 5 wherein the geometric volume is an ellipsoid.

7. The method of claim 1 wherein the growth criteria for adding voxels to the region is whether a voxel has an intensity level greater than a threshold.

8. The method of claim 1 wherein the growing of a region stops once a predetermined number of voxels is added to the region.

9. The method of claim 1 wherein the growth criteria for adding voxels to the region is whether a voxel has an intensity level greater than a threshold in a Laplacian-of-Gaussian volume.

10. The method of claim 1 further including the step of performing noise reduction on the volume created from the anatomical images.

11. The method of claim 1 further including the step of creating a distance map which tracks the distance of each voxel in the region from a predetermined location.

12. The method of claim 11 wherein the predetermined location is the seed voxel.

13. The method of claim 11 wherein the predetermined location is a heart.

14. The method of claim 11 wherein the predetermined location is a kidney, liver, spleen or brain.

15. The method of claim 1 further including the step of detecting variations in a width of the region.

16. The method of claim 1 wherein the region corresponds to a vessel volume.

17. The method of claim 1 wherein the region is a blood vessel.

18. The method of claim 1 wherein the first voxel distances are distances of the voxels in the region to the seed voxel.

19. The method of claim 1 wherein the first voxel distance is a distance of a voxel in the region to a heart or heart region.

20. The method of claim 1 wherein the second voxel distances are distances of a voxel in the region to nearest voxels outside the region.

21. The method of claim 1 wherein the step of processing a ratio further includes identifying as candidate nodules voxels resulting in ratio greater than '1'.

22. A computer system including software for identifying candidate nodules in a series of digital images of the lung:
- logic code for selecting a seed voxel from a volume created from the digital images;
- logic code for growing a region from the seed voxel, said region defined by a volume made up of voxels contiguous to the seed voxel and satisfying growth criteria;
- logic code for creating a first array having first array values that relate each voxel of the region to a first voxel distance;
- logic code for creating a second array having second array values that relate each voxel of the region to a second voxel distance; and
- logic code for processing a ratio of first array values to a corresponding second array values to determine one or more candidate nodule locations.

23. The computer system of claim 22 wherein the region is a blood vessel tree.

24. A method for detecting from anatomical images a candidate location of a blockage in a vessel comprising the steps of:
- selecting one or more seed voxels from a volume created from the anatomical images;
- growing a first region from s seed voxel, said region defined by a volume made up of voxels contiguous to the seed voxel and satisfying a first set of growth criteria;
- growing within the first region a second region, said second region defined by a volume made up of voxels contiguous with the seed voxels and satisfying a second set of growth criteria; and
- analyzing one or more portions of the first region that are not included in the second region based on the voxel intensities for voxels in the one or more portions.

* * * * *

UNITED STATES PATENT AND TRADEMARK OFFICE
CERTIFICATE OF CORRECTION

PATENT NO. : 7,272,250 B2 Page 1 of 1
APPLICATION NO. : 09/993791
DATED : September 18, 2007
INVENTOR(S) : Alexander C. Schneider and Susan A. Wood It is certified that error appears in the above-identified patent and that said Letters Patent is hereby corrected as shown below:

In claim 24, Col. 12, line 31, replace "from s seed voxel" with --from a seed voxel--

Signed and Sealed this

Eleventh Day of December, 2007

JON W. DUDAS
*Director of the United States Patent and Trademark Office*